United States Patent
Ostgard et al.

(10) Patent No.: US 6,284,703 B1
(45) Date of Patent: Sep. 4, 2001

(54) FIXED BED CATALYSTS

(75) Inventors: Daniel Ostgard, Kleinostheim; Konrad Moebus, Haina-Loehlbach; Monika Berweiler, Maintal; Barbara Bender, Rodenbach; Gernot Stein, Erlensee, all of (DE)

(73) Assignee: Degussa-Huels Aktiengesellschaft, Frankfurt/M. (DE)

( * ) Notice: Subject to any disclaimer, the term of this patent is extended or adjusted under 35 U.S.C. 154(b) by 0 days.

(21) Appl. No.: 09/368,571

(22) Filed: Aug. 5, 1999

(30) Foreign Application Priority Data

Jul. 31, 1999 (DE) .............................................. 199 36 135

(51) Int. Cl.⁷ .......................... C07C 35/06; C07C 24/07; B01J 25/00; B01J 25/02; B01J 25/04
(52) U.S. Cl. .......................... 502/301; 568/885; 568/838
(58) Field of Search .......................... 526/907; 502/301; 568/838, 885

(56) References Cited

U.S. PATENT DOCUMENTS

| | | |
|---|---|---|
| 4,043,946 | 8/1977 | Sanker et al. |
| 4,089,812 * | 5/1978 | O'Hare et al. .................... 252/466 J |
| 4,826,799 * | 5/1989 | Cheng et al. ......................... 502/301 |
| 4,895,994 * | 1/1990 | Cheng et al. ......................... 585/270 |

FOREIGN PATENT DOCUMENTS

| | | | | |
|---|---|---|---|---|
| 3537247 A1 | * | 4/1987 | (DE) | .............. C07C/85/11 |
| 4446907 A1 | * | 7/1996 | (DE) | .............. B01J/37/08 |
| 19640554 A1 | * | 4/1998 | (DE) | .............. C07D/307/88 |
| 0 648 534 A1 | * | 4/1995 | (EP) | .............. B01J/25/00 |
| 0 734 765 A1 | * | 10/1996 | (EP) | .............. B01J/25/02 |
| 0 880 996 A1 | * | 12/1998 | (EP) | .............. B01J/25/00 |

OTHER PUBLICATIONS

T. Beisekov, et al., Chemical Abstracts, vol. 125, No. 12, AN 125:145585, pp. 175, "Hydrogenation of Furfural on Promoted Nickel Catalysts Under Hydrogen Pressure," Sep. 16, 1996.

* cited by examiner

Primary Examiner—Johann Richter
Assistant Examiner—Brian J. Davis
(74) Attorney, Agent, or Firm—Oblon, Spivak, McClelland, Maier & Neustadt, P.C.

(57) ABSTRACT

A shaped, activated, fixed-bed Raney metal catalyst prepared by a method comprising preparing a mixture of powders comprising at least one catalyst alloy of (1) at least one catalytically active Raney process metal, a leachable alloy component and optionally a promoter, (2) at least one binder containing at least one pure Raney metal and (3) a moistening agent. Shaping, calcining and activating said catalyst and doping said catalyst with rhenium.

30 Claims, No Drawings

FIXED BED CATALYSTS

BACKGROUND OF THE INVENTION

Field of the Invention

The present invention relates to fixed bed catalysts and their use for the hydrogenation of saturated and unsaturated esters.

DESCRIPTION OF THE BACKGROUND

Activated metal catalysts are known in the field of chemical engineering as Raney catalysts. They are used, largely in powder form, for a large number of hydrogenation, dehydrogenation, isomerization reductive alkylation, reductive amination, and hydration reactions of organic compounds. These powdered catalysts are prepared from an alloy of a catalytically active metal, also referred to herein as a catalyst metal, with a further alloying component which is soluble in an alkali. Suitable catalytically active metals include nickel, cobalt, copper and iron. Aluminum is generally used as the alloying component which is soluble in an alkali, but other components may also be used, in particular, zinc or silicon or mixtures of either one of these elements with aluminum.

Powdered catalysts have the disadvantage that they can be used only in a batch process and, after the catalytic reaction, have to be separated from the reaction medium by costly sedimentation and/or filtration techniques. Therefore a variety of processes for preparing molded forms of the catalysts, which lead to activated metal fixed-bed catalysts after extraction of the aluminum have been disclosed. Thus, for example, coarse particulate Raney alloys, i.e., Raney alloys which have only been coarsely milled, can be prepared and these alloys can be activated by treatment with a caustic soda solution. Extraction and activation then occurs only in a surface layer, the thickness of which can be adjusted by the conditions used during extraction.

A substantial disadvantage of catalysts prepared by these known methods are the poor mechanical stability of the activated outer layer. Since only this outer layer of the catalysts is the catalytically active component, abrasion leads to rapid deactivation and renewed activation of deeper lying layers of alloy using caustic soda solution then leads at best to partial reactivation.

It is known that Re doped Pd (DE 25 19 817 A1)or Re doped Ru (WO 96/27436) supported catalysts are useful for the production of gamma-butyrolactone (GBL), tetrahydrofuran (THF), and 1,4-butanediol (BDO) by either maleic acid or maleic anhydride hydrogenation. These systems work as either powder or fixed bed catalysts at pressures of 138 bar or higher and temperatures of 250° C. or higher. In this respect, a system that performs this reaction at milder conditions would be a strong advantage. Copper-chromite is another catalyst system that has used for ester hydrogenation with some success (DE 39 03 029 A1).

EP 0 648 534 A1 describes shaped, activated Raney metal fixed-bed catalysts (Metalyst®) and their preparation. These catalysts avoid the disadvantages described above, i.e., the poor mechanical stability resulting from activating an outer layer. To prepare these catalysts, a mixture of powders consisting of a catalyst alloy and a binder are used, where the catalyst alloy contains at least one catalytically active catalyst metal and an extractable alloying component. The pure catalyst metals or mixtures thereof, which do not contain an extractable component, are used as the binder. The use of the binder in an amount of 0.5 to 20 weight percent with respect to the catalyst alloy, is essential in order to achieve sufficient mechanical stability after activation. After shaping the catalyst alloy and the binder with conventional shaping aids and pore producers, the freshly prepared items which are obtained are calcined at temperatures below 850° C. As a result of sintering within the finely divided binder, solid compounds are produced between the individual granules of the catalyst alloy. These compounds, in contrast to catalyst alloys, are non-extractable or only extractable to a small extent so that a mechanically stable structure is obtained even after activation without endangering the strength of the shaped item.

SUMMARY OF THE INVENTION

Accordingly, one object of the present invention is to provide fixed bed activated base metal catalysts that hydrogenate saturated and unsaturated esters under milder conditions than existing technologies with better activities and selectivities.

Briefly, this object and other objects of the present invention as hereinafter will become more readily apparent can be attained by a shaped, activated Raney metal fixed-bed catalyst prepared by a method comprising preparing a mixture of powders comprising at least one catalyst alloy of at least one catalytically active Raney process metal, a leachable alloy component and optionally a promoter, and at least one binder containing at least one pure Raney process metal, and a moistening agent, and optionally an additive selected from the group consisting of a shaping aid, lubricant, plasticizer, pore-producer, and mixtures thereof; homogenizing said mixture; shaping said mixture into a molded catalyst precursor which is not activated; calcining said molded catalyst precursor at a temperature below 850° C. to prepare a sintered catalyst precursor, and activating said sintered catalyst precursor by leaching said leachable alloy component with alkali until the leached and thereby activated outer layer has an adjustable thickness corresponding up to 70% or more of the molded form being activated, and subsequently washing the final catalyst; doping said catalyst with rhenium as a promoter after said activation and washing by introducing said catalyst into a rhenium solution. The pH of the Re solution may or may not be adjusted, and the temperature of the doping solution may vary from lower than room temperature to substantially higher temperatures. Moreover, the rhenium may be added to the unactivated alloy, the binder, or introduced in any other fashion that allows for its presence in the catalyst. The Re content can range from 0.01% Re to 30% Re, preferably from 0.01% to 15%, more preferably from 0.01% to 10% by weight of the catalyst.

DETAILED DESCRIPTION OF THE PREFERRED EMBODIMENTS

The fixed bed catalysts of the invention have the advantage that Re doped metal catalysts promote the hydrogenation of maleic acid or maleic anhydride to gamma-butyrolactone, tetrahydrofuran or 1,4-butanediol at a temperature of 200° C. and a pressure of 80 bar. Additionally the present catalyst is able to hydrogenate fatty esters to the corresponding fatty alcohols at higher activities and selectivities than the standard copper chromite catalysts.

Preferred Raney process metals include nickel, cobalt, copper, or combination thereof and the leachable alloying components include aluminum, zinc, silicon, or combinations thereof. These metals are generally leached by an alkali such as NaOH. The ratio by weight of Raney process metal to leachable alloying component in the catalyst alloy is in the range from 10:90 to 90:10, as is normally the case with Raney alloys. The Raney process metal used as binder, in a real practical application, does not have to be the same as the catalyst metal present in the catalyst alloy. Rather, it is possible to combine different Raney process metals with each other as well as with promoter metals, in the catalyst alloy and as binder, offering a further important degree of freedom when adjusting the catalytic properties to the particular catalytic process. Thus the binder employed in the present invention can be nickel, cobalt, copper, iron, and optionally promoter metals. Generally any of the metals used for making Raney metal catalysts are suitable. The binder metal is employed in an unreachable and unadulterated form.

Catalyst alloy and binder are processed in the form of powders, typically with the addition of moistening agents and optionally with the addition of conventional additives such as shaping aids, lubricants, plasticizers, and optionally pore-producers to give a moldable material. Any materials conventionally used for these purposes may be used as the shaping aid, lubricant, plasticizer and pore-producer. A number of suitable materials for this purpose are disclosed in U.S. Pat. No. 4,826,799; 3,404,551; and 3,351,495 all of which are incorporated by reference in their entirety. Waxes such as, for example, wax C micropowder PM from Hoechst AG, greases such as magnesium or aluminum stearates, or polymers which contain carbohydrates such as tylose (methylcellulose) are preferably used for the above purposes.

The solids in the mixture are carefully homogenized in suitable conventional mixers or kneaders with the addition of a moistening agent. Water, alcohols, glycols, polyether glycols or mixtures thereof are suitable as moistening agents as is well known in the art.

The primary particle size ranges of the powders of catalyst alloy and binder used are essentially unchanged during homogenization. That is, no milling takes place.

The purpose of this preliminary treatment with the moistening agent and additives is to prepare the mixture for the subsequent shaping process. Extrusion, pelleting and compression may be used, for example, for the shaping process employing conventional equipment known for such purposes.

The type and sequence of incorporation of additives depends on the shaping process to be used. Extrusion requires a plastic material with a specific viscosity, whereas a material which is free-flowing and which can be readily metered out is required for pelleting. The techniques to be used for this purpose, such as, for example, agglomeration to produce a free-flowing powder or adjustment to the correct viscosity for extrusion, are known as a matter of routine to the person skilled in the art. It is only important that the primary particle size ranges of the catalyst powder and binder powder are essentially unchanged by the preliminary treatment.

Any shapes which are conventional in the catalyst field are suitable as molded items. Spheres, rings, spoked rings or pellets may be produced, depending on the requirements of the particular application.

The molded structures are optionally dried to constant weight at temperatures ranging from 80° C. to 120° C. and then calcined at temperatures below 850° C., preferably from 500° C. to 700° C., in air in continuous or batch operated kilns such as rotary kilns or stationary kilns. The organic additives then burn off and leave behind a corresponding porous system.

The porous structure and pore volume of the catalysts can be varied over a wide range by suitable selection of the pore-producing additives. The final pore structure which is developed and the pore volume are also affected by the particle sizes of the powders of catalyst alloy and binder employed.

The structure of the molded catalyst can be adapted to the requirements for a particular catalytic process by appropriate selection of the parameters mentioned.

During calcination of the molded catalyst structures, the catalyst alloy powder and binder powder sinter together and provide the molded catalyst structures with high mechanical stability and good resistance to abrasion. Typically, the hardness of cylindrical pellets after calcination ranges from 200 to 300 N (measured radially in accordance with ASTM D 417982).

After calcination the molded catalyst structures are activated by leaching the aluminum with caustic soda solution. A 20% strength sodium hydroxide solution warmed to 80° C. can be used for this purpose. In this case, treatment for 2 hours leads to an active outer layer with a thickness of about 0.1 to 1 mm. Surprisingly, it has been shown that the hardness is actually slightly increased by leaching, in the case of pellets to values of more than 300 N.

These properties are closely connected with the pure Raney process metal employed as binder which is not dissolved during leaching and thus in the sintered product forms stable bonds between the individual alloyed particles. According to German Patent DE 197 218 98.9 (Freund, Berweiler, Bender and Kempf; 1998) the use of a metallic binder for the production of Metalyst® can be avoided if the phase domains of the alloy are sufficiently small enough. The size of the phase domains can be controlled by the cooling rate and method employed for cooling of the alloy. Hence, the use of a binder in the invention of this patent is optional and the technology of DE 197 218 98.9 is applicable to this catalyst.

The choice of metals used as binder may contribute to the catalytic activity. Restricting the temperature of calcination to values below 850° C. prevents the formation of alpha-aluminum oxide as shown by X-ray diffraction analysis of the calcined material. Any γ-aluminum oxide which is formed is removed by dissolution from the catalyst structure when activating the catalyst with caustic soda solution.

The lack of α-aluminum oxide in the catalyst becomes clearly noticeable on activation. Whereas catalysts of the present invention can be activated under quite mild conditions (20% NaOH, 80° C.) within only 2 hours, the temperature of the alkaline solution has to be raised and the activation time extended when activating catalysts bonded with α-aluminum oxide (according to U.S. Pat. No. 4,826,799) in order to obtain an active outer layer of the same thickness.

To prepare the catalyst of the present invention, the average particle sizes of the catalyst alloy powder and of the binder, and also the ratio by weight of catalyst alloy powder to binder, can be varied over a wide range. Since the binder also contributes to the catalytic activity, but it cannot be activated by extracting aluminum, its possible contribution to the catalytic activity is limited. Therefore its proportion in the catalyst should be kept as small as possible.

Ratios by weight of catalyst alloy powder to binder range from 100:20 to 100:0.5 have proven to be useful. The particle size of the binder should be smaller than the particle size of the catalyst alloy powder. Particles of binder can then be regarded as small bridges between the larger alloyed particles. It has been found that the hardness of the final catalyst structure increases within certain limits with decreasing particle size of the binder. Reasonable activity values are obtained when the powder of the catalyst alloy has an average particle size ranging from 10 and to 500 μm.

When the catalyst is doped with rhenium, it is expedient to conduct doping only after activating the catalyst. For this, the final catalyst is introduced into a rhenium solution, e.g., perrhenic acid. The amount of rhenium and the time needed for its addition can be controlled by adjusting the pH and the temperature of the rhenium solution. A specific amount of the rhenium compound is adsorbed by the catalyst, depending on the type of treatment, e.g. up to 20% by weight.

An aspect of the invention is a process for preparing the shaped Raney metal fixed-bed catalyst. The process consists essentially of preparing a mixture of powders consisting essentially of at least one catalyst alloy and optionally one binder, and a moistening agent. An additive selected from the group consisting of a shaping aid, lubricant, plasticizer, pore—producer, and mixtures thereof, is optionally included, and said catalyst alloy consists essentially of at least one Raney process metal as the catalytically active component, a leachable alloy component and optionally a promoter. The optional binder consists essentially of at least one Raney process metal. Processing continues by homogenizing the mixture, shaping the mixture to give a molded catalyst precursor which is not activated, calcining the molded catalyst precursor at a temperature less than 850° C. to prepare a sintered catalyst precursor, and activating the sintered catalyst precursor by leaching the leachable alloy component with alkali until the leached and thereby activated outer layer has a thickness of 0.05 to 1 mm or higher; optionally subsequently washing the final catalyst. Rhenium, after activating and washing the catalyst is added by introducing the catalyst into a rhenium solution, where rhenium deposition is controlled by the temperature and pH of the rhenium solution.

Another aspect of the invention is the use of the rhenium doped Raney metal fixed-bed catalyst for the hydrogenation of unsaturated and saturated esters. An example of such a process is the hydrogenation of maleic anhydride to γ-butyrolactone, tetrahydrofuran, 1,4-butanediol under mild conditions. Moreover, it has been found that the present catalyst is an excellent catalyst for the hydrogenation of fatty esters to fatty alcohols.

EXAMPLES

Comparison Example 1

A commercially available 2% Pd catalyst on 4 mm carbon extrudates is doped with 0.5% Re by treating it in a perrhenic acid solution whose pH is adjusted to 10.5 with sodium hydroxide before introducing the catalyst to the solution. The treatment continued until no rhenium remained in the rhenium solution. Maleic anhydride is hydrogenated in the presence of the catalyst as described in Application Example 1 (infra) yielding 10.5% gamma-butyrolactone, 0.0% tetrahydrofuran and 0.0% 1.4-butanediol after a reaction time of 5 hours.

Example 1

A free-flowing, pelletable catalyst mixture is prepared by the method described in EP 0 648 534 A1 for a catalyst consisting of 1000 g of 50%Ni and 50%Al alloy powder, 7.5 g of pure nickel powder (99% Ni, and d50=21 μm), and 50 g of ethylene bis-stearoylamide. Tablets with a diameter of 4 mm and a thickness of 4 mm are compressed from this mixture. The shaped items are calcined for 2 h at 700° C. The tablets are activated in 20% strength caustic soda solution for 2 hours at 80° C. after calcination. This catalyst is doped to the level of 0.45% Re by exposing the catalyst for 48 h to a stirred perrhenic acid solution that is adjusted to a pH of 10.5 before adding the catalyst. Maleic anhydride is hydrogenated in the presence of the catalyst as described in Application Example 1 (infra) yielding 71.6% gamma butyrolactone, 4.7% tetrahydrofuran, and 1.3% 1.4-butanediol after a reaction time of 5 hours.

Comparison Example 2

Commercially available copper chromite extrudates from Mallinckrodt were used as a comparative technology for the hydrogenation of fatty esters. When the catalyst is used as described in Example 2, this catalyst produces 20.78% fatty alcohol with a saponification number of 136.6 after 300 minutes of reaction time at 230° C. The color of the reactant at this time was a bluish-green indicating the presence of dissolved metals.

Unsaturated ester is hydrogenated in the presence of the catalyst as described in Application Example 3 (infra) yielding 20.5% fatty alcohol with a saponification number of 143.5 after 1230 minutes of reaction time at 200° C.

Example 2

A free-flowing, pelletable catalyst mixture is prepared by the procedure described in EP 0 648 534 A1 for a catalyst consisting of 1000 g of 50%Ni and 50%Al alloy powder, 7.5 g of pure nickel powder (99%Ni, and d50=21 μm), and 50 g of ethylene bis-stearoylamide. Tablets with a diameter of 4 mm and a thickness of 4 mm are compressed from this mixture. The shaped items are calcined for 2 h at 700° C. The tablets are activated in 20% strength caustic soda solution for 2 hours at 80° C. after calcination. This catalyst is doped to the level of 2.0% Re by exposing the catalyst for 100 h to a stirred perrhenic acid solution that is adjusted to a pH of 10.5 before adding the catalyst. Maleic anhydride is hydrogenated in the presence of the catalyst as described in Application Example 1 (infrared) yielding 55% gamma-butyrolactone, 14.2% tetrahydrofuran, and 1.3% 1,4-butanediol after a reaction time of 5 hours.

Example 3

A free-flowing, pelletable catalyst mixture is prepared by the procedure described in EP 0 648 534 A1 for a catalyst consisting of 1000 g of 50%Ni and 50%Al alloy powder, 7.5 g of pure nickel powder (99%Ni, and d50=21 μm), and 50 g of ethylene bis-stearoylamide. Tablets with a diameter of 4 mm and a thickness of 4 mm are compressed from this mixture. The shaped items are calcined for 2 h at 700° C. The tablets are activated in 20% strength caustic soda solution for 2 hours at 80° C. after calcination. This catalyst is doped to the level of 4.0% Re by exposing the catalyst for 192 h to a stirred perrhenic acid solution that is adjusted to a pH of 10.5 before adding the catalyst. Maleic anhydride is hydrogenated in the presence of the catalyst as described in Application Example 1 (infra) yielding 40% gamma-butyrolactone, 3.5% tetrahydrofuran, and 26.25% 1.4-butanediol after a reaction time of 5 hours.

Example 4

A free-flowing, pelletable catalyst mixture is prepared by the procedure described in EP 0 648 534 A1 for a catalyst consisting of 1000 g of 50%Ni and 50%Al alloy powder, 7.5 g of pure nickel powder (99%Ni, and d50=21 μm), and 50 g of ethylene bis-stearoylamide. Tablets with the diameter of 4 mm and a thickness of 4 mm are compressed from this mixture. The shaped items are calcined for 2 h at 700° C. The tablets are activated in 20% strength caustic soda solution for 2 hours at 80° C. after calcination. This catalyst is doped to the level of 6.0% Re by exposing the catalyst for 240 h to a stirred perrhenic acid solution that is adjusted to a pH of 10.5 before adding the catalyst. Maleic anhydride is hydrogenated in the presence of the catalyst as described in Application Example 1 (infra) yielding 25.9% gamma-butyrolactone, 3.71% tetrahydrofuran, and 26.9% 1,4-butanediol after a reaction time of 5 hours.

Example 5

A free-flowing, pelletable catalyst mixture is prepared by the procedure described in EP 0 648 534 A1 for a catalyst consisting of 1000 g of 50%Cu and 50%Al alloy powder, 430 g of pure nickel powder (d50=23 μm), and 50 g of ethylene bis-stearoylamide. Tablets with a diameter of 3 mm and a thickness of 3 mm are compressed from this mixture. The shaped items are calcined for 6 h at 700° C. The tablets are activated in 20% strength caustic soda solution for 2 h at 80° C. after calcination. When used according to the procedure of Application Example 2 (infra), this catalyst produced 3.32% fatty alcohol with a saponification number of 176.0 after 300 minutes of reaction time at 230° C. The color of the reactant at this time was white indicating the absence of dissolved metals. Although this catalyst already performs similarly to (if not slightly better) the activated nickel catalyst, its activity can be improved by using less binder and decreasing the severity of its calcination. Thus Re doping can improve this catalyst system at least to the same extent as the activated Ni catalyst.

Comparison Example 3

A free-flowing, pelletable catalyst mixture is prepared by the procedure in EP 0 648 534 A1 for a catalyst consisting of 1000 g of 50%Ni and 50%Al alloy powder, 7.5 g of pure nickel powder (99%Ni, and d50=21 μm), and 50 g of ethylene bis-stearoylamide. Tablets with the diameter of 3 mm and a thickness of 3 mm are compressed from this mixture. The shaped items are calcined for 2 h at 700° C. The tablets are activated in 20% strength caustic soda solution for 2 h at 80° C. after calcination. When the catalyst is used in the procedure described in Application Example 2, a yield of 1.92% fatty alcohol with a saponification number of 174.2 after 300 minutes of reaction time at 230° C. is obtained. The color of the reactant at this time was white indicating the absence of dissolved metals.

Example 6

A free-flowing, pelletable catalyst mixture is prepared by the procedure described in EP 0 648 534 A1 for a catalyst consisting of 1000 g of 50%Ni and 50%Al alloy powder, 7.5 g of pure nickel powder (99%Ni, and d50=21 μm), and 50 g of ethylene bis-stearoylamide. Tablets with the diameter of 3 mm and a thickness of 3 mm are compressed from this mixture. The shaped items are calcined for 2 h at 700° C. The tablets are activated in 20% strength caustic soda solution for 2 h at 80° C. after calcination. This catalyst is doped to a level of 3.0% Re by exposing the catalyst for 72 hours to a stirred perrhenic acid solution that is adjusted to the pH of 10.5 before adding the catalyst. When the catalyst is used in the procedure described in Application Example 2, a yield of 25.39% fatty alcohol with a saponification number of 107.9 after 300 minutes of reaction time at 230° C. The color of the reactant at this time was white indicating the absence of dissolved metals. When the catalyst is used in the procedure described in Application Example 3, a yield of 63.85% fatty alcohol with a saponification number of 61.2 after 1230 minutes of reaction time at 200° C. is obtained.

Comparison Example 4

A free-flowing, pelletable catalyst mixture is prepared by the procedure described in EP 0 648 534 A1 for a catalyst consisting of 1000 g of 40.0%Ni, 58.5%Al, 1.0%Cr, and 0.5%Fe alloy powder; 7.5 g of pure nickel powder (99%Ni, and d50=21 μm); and 50 g of ethylene bis-stearoylamide. Tablets with the diameter of 3 mm and a thickness of 3 mm are compressed from this mixture. The shaped items are calcined for 2 h at 700° C. The tablets are activated in 20% strength caustic soda solution for 2 h at 80° C. after calcination. When the catalyst is used in the procedure described in Application Example 2, this catalyst produced 6.72% fatty alcohol with a saponification number of 160.7 after 300 minutes of reaction time at 230° C. is obtained. The color of the reactant at this time was white indicating the absence of dissolved metals.

Example 7

A free-flowing, pelletable catalyst mixture is prepared by the procedure described in EP 0 648 534 A1 for a catalyst consisting of 1000 g of 40.0%Ni, 58.5%Al, 1.0%Cr, and 0.5%Fe alloy powder; 7.5 g of pure nickel powder (99%Ni, and d50=21 μm); and 50 g of ethylene bis-stearoylamide. Tablets with a diameter of 3 mm and a thickness of 3 mm are compressed from this mixture. The shaped items are calcined for 2 h at 700° C. The tablets are activated in 20% strength caustic soda solution for 2 h at 80° C. after calcination. This catalyst is doped to a level of 3.0% Re by exposing the catalyst for 72 hours to a stirred perrhenic acid solution that is adjusted to a pH of 10.5 before adding the catalyst. When the catalyst is used in the procedure described in Application Example 2, a yield of 34.2% fatty alcohol with a saponification number of 98.8 after 300 minutes of reaction time at 230° C. is obtained. The color of the reactant at this time was white indicating the absence of dissolved metals.

Application Example 1

The catalytic activities of the catalysts of Comparison Example 1 and of Examples 1 to 4 are compared in the abilities of the catalysts to hydrogenate maleic anhydride. For this purpose, 7 g of maleic anhydride and 250 g of 1,4-dioxane are placed in a stirred autoclave with a capacity of 0.5 l and outfitted with a gas stirrer spinning at 1000 rpm. An amount of catalyst (in grams) is suspended each time in a stirred autoclave using a catalyst basket so that the catalyst material is thoroughly washed by the reactant/solvent mixture before hydrogen is introduced into the reactor. Hydrogenation is performed at a hydrogen pressure of 80 bar, the temperature of 200° C., and the reaction is stopped after 5 hours. Samples are withdrawn after 2 and 5 h and analyzed by gas chromatography to calculate catalyst activity and selectivity. The results of these tests are given in Table 3.

Application Example 2

The catalytic activities of the catalysts of Comparison Examples 2–4 and Examples 5–7 are compared in the abilities of the catalysts to hydrogenate a mixture of saturated and unsaturated C-16 and C-18 esters to the fatty alcohols. The reactant was a commercial feed consisting of approximately 70% C-18 and 30% C-16 methyl esters with about 60% of the total feedstock being unsaturated. The feed also contained a very small amount of C-12, C-14, and C-20 methyl esters where the sum total of these other esters is less than 1%. The hydrogenation of 500 ml of the above mentioned fatty ester feedstock is conducted with 72 g of catalyst at 200 bar and 230° C. in a 1 liter stirred autoclave outfitted with a bubble-stirrer and a catalyst basket. A sample is removed after 300 minutes of reaction for analysis by gas chromatography and determination of its saponification number. The saponification number is determined by mixing 2.0 g (±0.1 mg) of the hydrogenation sample with 50 ml of an ethanolic 0.5 N KOH solution and refluxing it at the solution's boiling point for 60 minutes. A 1.0% phenolphthalien solution is added given to the warm solution and the solution is titrated with a standard 0.5 N HCl solution to determine the remaining amount of KOH. A blind experiment without the hydrogenation sample is conducted at the same time under the same conditions for reference. The saponification number is equal to the mg of KOH that is needed to saponify one gram of the fatty ester mixture where a higher number indicates that the mixture contains a higher percentage of ester. In the comparisons used here, a higher saponification number means that less of the fatty ester was converted to the corresponding fatty alcohol during the hydrogenation. The data for these experiments are listed in Table 1.

Application Example 3

The catalytic activity of the catalysts from Comparison Example 2 and Example 6 are also compared in the abilities of the catalysts to hydrogenate the mixture of saturated and unsaturated C-16 and C-18 esters mentioned above in Application Example 2 to alcohols at the same conditions with the exception being the reaction temperature of 200° C. The sample times for this experiment are 300 and 1230 minutes for analysis by gas chromatography and determination of the saponification number (as described above). The data of these experiments are listed in Table 2.

TABLE 1

Analysis of the hydrogenation samples after 300 minutes of reaction at the temperature of 230° C.

| Catalyst | Saponification Number | Gas Chromatograph Determined % Fatty Alcohol | Product Color |
|---|---|---|---|
| CE2 | 136.6 | 20.78 | Blueish-green |
| CE3 | 174.2 | 1.92 | White |
| CE4 | 160.7 | 6.72 | White |
| E5 | 176.0 | 3.32 | White |
| E6 | 107.9 | 25.39 | White |
| E7 | 98.8 | 34.2 | White |

TABLE 2

Analysis of the hydrogenation samples after 300 and 1230 minutes of reaction at the temperature of 200° C.

| | Reaction time = 300 minutes | | Rection Time = 1230 minutes | |
|---|---|---|---|---|
| Catalyst | Saponification Number | Gas Chromatograph Determined % Fatty Alcohol | Saponification Number | Gas Chromatograph Determined % Fatty Alcohol |
| CE2 | — | 3.16 | 143.5 | 20.5 |
| E6 | 144.7 | 20.79 | 61.2 | 63.85 |

TABLE 3

The Hydrogenation of Maleic Anhydride to Gamma Butyrolactone, Tetrahydrofuran, and/or 1,4-butanediol according to Application Example 1.

| Catalyst | % Re | Reaction Time, h | % Maleic Anhydride | % Gamma Butyrolactone | % Tetrahydrofuran | % 1,4-butanediol |
|---|---|---|---|---|---|---|
| CE1 | 0.5 | 2 | 0.1 | 4.7 | 0.0 | 0.0 |
| | | 5 | 0.1 | 10.5 | 0.0 | 0.0 |
| E1 | 0.45 | 5 | 0.0 | 71.6 | 4.7 | 1.3 |
| E2 | 2.0 | 2 | 0.1 | 60.4 | 3.3 | 0.5 |
| | | 5 | 0.1 | 55.0 | 14.2 | 1.3 |
| E3 | 4.0 | 2 | 1.33 | 49.5 | 1.06 | 9.2 |
| | | 5 | 0.0 | 40.1 | 3.5 | 26.25 |
| E4 | 6.0 | 2 | 2.34 | 60.3 | 0.96 | 11.2 |
| | | 5 | 0 | 25.9 | 3.71 | 26.9 |

What is claimed is:
1. A shaped, activated, fixed-bed Raney metal catalyst prepared by a method comprising:
(i) preparing a mixture of powders comprising at least one catalyst alloy of (1) at least one catalytically active Raney process metal, a leachable alloy component and optionally a promoter, (2) at least one binder containing at least one pure Raney process metal, and (3) a moistening agent,
(i-a) homogenizing said mixture,
(i-b) shaping said mixture into a molded catalyst precursor which is not activated,
(i-c) calcining said molded catalyst precursor at a temperature below 850° C., thereby obtaining a sintered catalyst precursor,
(i-d) activating said sintered catalyst precursor by leaching said leachable alloy component with alkali until the leached, and thereby activated outer layer has a thickness of 0.05 to 1 mm, and
(i-e) subsequently washing the final catalyst; and
(ii) doping said catalyst with rhenium as a promoter after said activation by introducing said catalyst into a perrhenic acid solution or a solution of a Re salt, for a sufficient period of time to dope the catalyst completely with the rhenium in said perrhenic acid solution.
2. The Raney metal catalyst of claim 1, wherein said mixture of powders (i) further comprises at least one additive selected from the group consisting of a shaping aid, lubricant, plasticizer, pore-producer and mixtures thereof.
3. A shaped, activated, fixed-bed Raney metal catalyst prepared by a method comprising:
(i) preparing a mixture of powders comprises at least one catalyst alloy of (1) at least one catalytically active Raney process metal, a leachable alloy component and optionally a promoter, (2) at least one binder containing at least one Raney process metal, and (3) a moistening agent, (i-a) homogenizing said mixture, (i-b) shaping said mixture into a molded catalyst precursor which is not activated, (i-c) calcining said molded catalyst precursor at a temperature below 850° C., thereby obtaining a sintered catalyst precursor, and (i-d) activating said sintered catalyst precursor by leaching said leachable alloy component with alkali until the leached, and thereby activated outer layer, has a thickness of 0.05 to 1 mm; and (ii) doping said catalyst with rhenium as a promoter after said activation by introducing said catalyst into a perrhenic acid solution, of an initially adjusted pH, for a sufficient period of time to dope the catalyst completely with the rhenium in said perrhenic acid solution.

4. The Raney metal catalyst of claim 3, wherein said mixture of powders (i) further comprises at least one additive selected from the group consisting of a shaping aid, lubricant, plasticizer, pore-producer and mixtures thereof.

5. The Raney metal catalyst of claim 3, which further comprises washing (i-e) said activated, sintered catalyst precursor (i-d).

6. The Raney metal catalyst of claim 1 or 3, wherein said binder contains Re.

7. The Raney metal catalyst of claim 1 or 3, wherein said catalyst alloy contains Re.

8. The Raney metal catalyst of claim 1 or 3, wherein the Re content ranges from 0.01% to 30% by weight, based on the catalyst.

9. The Raney metal catalyst of claim 7, wherein the Re content ranges from 0.01% to 10% by weight, based on the catalyst.

10. The Raney metal catalyst of claim 1 or 3, wherein the Raney metal is Ni.

11. The Raney metal catalyst of claim 1 or 3, wherein the Raney metal is Cu.

12. The Raney metal catalyst of claim 1 or 3 which further comprises doping the catalyst with 0.01–5% by weight chromium in combination with 0.01–5% by weight iron, each percentage based on the weight of catalyst, before or after doping of the catalyst with Re.

13. The Raney metal catalyst of claim 10, which further comprises doping the catalyst with 0.01–5% by weight chromium in combination with 0.01–5% by weight iron, each percentage based on the weight of catalyst, before or after doping of the catalyst with Re.

14. The Raney metal catalyst of claim 1 or 3, which further comprises doping the catalyst with 0.01–5% by weight chromium, based on the weight of catalyst, before or after doping of the catalyst with Re.

15. The Raney metal catalyst of claim 1 or 3, which further comprises doping the catalyst with 0.01–5% by weight iron, based on the weight of catalyst, before or after doping of the catalyst with Re.

16. The Raney metal catalyst of claim 1 or 3, which further comprises doping the catalyst with a promoter selected from the group consisting of Ti, Zr, V, Ta, Mo, W, Ru, Pd, Pt, Cu, Zn or Co before or after doping of the catalyst with Re.

17. The Raney metal catalyst of claim 1 or 3, wherein deposition of the Re is controlled by the pH of the doping Re containing solution.

18. The Raney metal catalyst of claim 1 or 3, wherein deposition of the Re is controlled by the temperature of the doping Re containing solution.

19. The Raney metal catalyst of claim 1 or 3, wherein deposition of the Re is controlled by both the pH and the temperature of the doping Re containing solution.

20. A shaped, activated, fixed-bed Raney metal catalyst prepared by a method comprising:

(i) preparing a mixture of powders comprising at least one catalyst alloy of (1) at least one catalytically active Raney process metal, a leachable alloy component and optionally a promoter and (2) a moistening agent, (i-a) homogenizing said mixture, (i-b) shaping said mixture into a molded catalyst precursor which is not activated, (i-c) calcining said molded catalyst precursor at a temperature below 850° C., thereby obtaining a sintered catalyst precursor, (i-d) activating said sintered catalyst precursor by leaching said leachable alloy component with alkali until the leached, and thereby activated outer layer has a thickness of 0.05 to 1 mm, and (i-e) subsequently washing the final catalyst; and (ii) doping said catalyst with rhenium as a promoter after said activation by introducing said catalyst into a perrhenic acid solution for a sufficient period of time to dope the catalyst completely with the rhenium in said perrhenic acid solution.

21. A shaped, activated, fixed-bed Raney metal catalyst prepared by a method comprising:

(i) preparing a mixture of powders comprising at least one catalyst alloy of (1) at least one catalytically active Raney process metal, a leachable alloy component and optionally a promoter and (2) a moistening agent, (i-a) homogenizing said mixture, (i-b) shaping said mixture into a molded catalyst precursor which is not activated, (i-c) calcining said molded catalyst precursor at a temperature below 850° C., thereby obtaining a sintered catalyst precursor, and (i-d) activating said sintered catalyst precursor by leaching said leachable alloy component with alkali until the leached, and thereby activated outer layer, has a thickness of 0.05 to 1 mm; and (ii) doping said catalyst with rhenium as a promoter after said activation by introducing said catalyst into a perrhenic acid solution, of an initially adjusted pH, for a sufficient period of time to dope the catalyst completely with the rhenium in said perrhenic acid solution.

22. A method of hydrogenating an ester, comprising:

hydrogenating a saturated or unsaturated ester in the presence of the catalyst of claim 1 or 3 to its corresponding mono- or polyhydroxy saturated alcohol.

23. A method of hydrogenating an ester, comprising:

partially hydrogenating a saturated or unsaturated ester in the presence of the catalyst of claim 1 or 3 to its corresponding mono- or polyhydroxy saturated alcohol.

24. A method of hydrogenating maleic anhydride, comprising:

hydrogenating maleic anhydride in the presence of the catalyst of claim 1 or 3 thereby yielding γ-butyrolactone, tetrahydrofuran and 1,4-butanediol.

25. A method of hydrogenating fatty esters, comprising:
hydrogenating fatty esters in the presence of the catalyst of claim 1 or 3 thereby yielding fatty alcohols.

26. A method of hydrogenating fatty esters, comprising:
hydrogenating $C_{12-20}$-fatty esters in the presence of the catalyst of claim 1 or 3 thereby yielding $C_{12-20}$-fatty alcohols.

27. A method of hydrogenating fatty esters, comprising:
hydrogenating $C_{16-18}$-fatty esters in the presence of the catalyst of claim 1 or 3 thereby yielding $C_{16-18}$-fatty alcohols.

28. A method of hydrogenating maleic acid, comprising:
hydrogenating maleic acid in the presence of the catalyst of claim 1 or 3 thereby yielding γ-butyrolactone, tetrahydrofuran and 1,4-butanediol.

29. A shaped, activated, calcined fixed-bed Raney metal catalyst, comprising:

a leached and activated Raney metal alloy catalyst comprising at least one catalytically active Raney process metal, a leachable alloy component and at least one binder material containing pure Raney process metal, the alloy being impregnated with from 0.01 to 30 wt. % Re, and the catalyst having a leached and activated outer layer of a thickness of 0.05 to 1 mm and having a hardness of 200 to 300 N after calcination.

30. The catalyst of claim 29, wherein the content of Re ranges from 0.01 to 10 % by wt.

* * * * *